(12) United States Patent
Freeman et al.

(10) Patent No.: US 9,084,533 B2
(45) Date of Patent: *Jul. 21, 2015

(54) MULTISPECTRAL/HYPERSPECTRAL MEDICAL INSTRUMENT

(71) Applicant: Hypermed Imaging, Inc., Greenwich, CT (US)

(72) Inventors: Jenny E. Freeman, Chestnut Hill, MA (US); Edgar N. Lewis, Brookeville, MD (US)

(73) Assignee: Hypermed Imaging, Inc., Greenwich, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/872,913

(22) Filed: Apr. 29, 2013

(65) Prior Publication Data

US 2013/0237841 A1 Sep. 12, 2013

Related U.S. Application Data

(60) Continuation of application No. 13/303,107, filed on Nov. 22, 2011, now Pat. No. 8,463,366, which is a continuation of application No. 11/165,587, filed on Jun. 24, 2005, now Pat. No. 8,175,688, which is a (Continued)

(51) Int. Cl.
| | |
|---|---|
| *A61B 6/00* | (2006.01) |
| *A61B 5/00* | (2006.01) |
| *A61B 1/00* | (2006.01) |
| *A61B 1/05* | (2006.01) |

(52) U.S. Cl.
CPC .......... *A61B 5/0075* (2013.01); *A61B 1/00009* (2013.01); *A61B 1/05* (2013.01); *A61B 5/0084* (2013.01); *Y10S 128/92* (2013.01)

(58) Field of Classification Search
CPC combination set(s) only.
See application file for complete search history.

(56) References Cited

U.S. PATENT DOCUMENTS

| | | | |
|---|---|---|---|
| 4,515,165 | A | 5/1985 | Carroll |
| 4,817,623 | A | 4/1989 | Stoddart et al. |
| 4,902,136 | A | 2/1990 | Mueller et al. |

(Continued)

FOREIGN PATENT DOCUMENTS

| | | |
|---|---|---|
| EP | 0 063 431 | 10/1987 |
| EP | 0 783 867 | 2/2006 |

(Continued)

OTHER PUBLICATIONS

Afromowitz et al, Spectroscopy of burn wounds, University of Washington, May 5, 1992.*

(Continued)

*Primary Examiner* — Unsu Jung
*Assistant Examiner* — Saurel J Selkin
(74) *Attorney, Agent, or Firm* — Brett A. Lovejoy; Andrew J. Antczak; Morgan, Lewis & Bockius, LLP

(57) ABSTRACT

A medical instrument that comprises: a first-stage optic responsive to a tissue surface of a patient; a spectral separator optically responsive to the first stage optic and having a control input; an imaging sensor optically responsive to the spectral separator and having an image data output; and a diagnostic processor having an image acquisition interface with an input responsive to the imaging sensor and a filter control interface having a control output provided to the control input of the spectral separator.

20 Claims, 3 Drawing Sheets

Related U.S. Application Data division of application No. 09/182,898, filed on Oct. 30, 1998, now Pat. No. 6,937,885.

(60) Provisional application No. 60/093,041, filed on Nov. 10, 1997.

(56) References Cited

U.S. PATENT DOCUMENTS

| | | | |
|---|---|---|---|
| 5,003,979 A * | 4/1991 | Merickel et al. | 600/410 |
| 5,016,173 A * | 5/1991 | Kenet et al. | 382/128 |
| 5,079,698 A | 1/1992 | Grenier et al. | |
| 5,104,392 A | 4/1992 | Kittrell et al. | |
| 5,125,404 A | 6/1992 | Kittrell et al. | |
| 5,140,989 A | 8/1992 | Lewis et al. | |
| 5,174,297 A | 12/1992 | Daikuzono | |
| 5,213,105 A | 5/1993 | Gratton et al. | |
| 5,216,484 A | 6/1993 | Chao et al. | |
| 5,217,013 A | 6/1993 | Lewis et al. | |
| 5,307,813 A | 5/1994 | Young | |
| 5,318,023 A | 6/1994 | Vari et al. | |
| 5,318,024 A | 6/1994 | Kittrell et al. | |
| 5,341,805 A | 8/1994 | Stavridi et al. | |
| 5,349,961 A | 9/1994 | Stoddart et al. | |
| 5,353,790 A | 10/1994 | Jacques et al. | |
| 5,377,003 A | 12/1994 | Lewis et al. | |
| 5,377,676 A | 1/1995 | Vari et al. | |
| 5,421,337 A | 6/1995 | Richards-Kortum et al. | |
| 5,452,723 A | 9/1995 | Wu et al. | |
| 5,456,252 A | 10/1995 | Vari et al. | |
| 5,461,477 A | 10/1995 | Marinelli et al. | |
| 5,507,287 A | 4/1996 | Palcic et al. | |
| 5,528,368 A | 6/1996 | Lewis et al. | |
| 5,539,517 A | 7/1996 | Cabib et al. | |
| 5,553,614 A | 9/1996 | Chance | |
| 5,587,585 A | 12/1996 | Eisen et al. | |
| 5,590,660 A | 1/1997 | MacAulay et al. | |
| 5,591,981 A | 1/1997 | Heffelfinger et al. | |
| 5,596,986 A * | 1/1997 | Goldfarb | 600/323 |
| 5,606,413 A | 2/1997 | Bellus et al. | |
| 5,647,368 A | 7/1997 | Zeng et al. | |
| 5,678,550 A | 10/1997 | Bassen et al. | |
| 5,697,373 A | 12/1997 | Richards-Kortum | |
| 5,733,739 A | 3/1998 | Zakim et al. | |
| 5,813,987 A | 9/1998 | Modell et al. | |
| 5,864,397 A | 1/1999 | Vo-Dinh | |
| 5,938,617 A | 8/1999 | Vo-Dinh | |
| 5,991,653 A | 11/1999 | Richards-Kortum | |
| 6,008,492 A | 12/1999 | Slater et al. | |
| 6,640,132 B1 * | 10/2003 | Freeman et al. | 600/476 |
| 6,937,885 B1 | 8/2005 | Lewis et al. | |

FOREIGN PATENT DOCUMENTS

| | | |
|---|---|---|
| GB | 2 300 045 | 6/1999 |
| JP | 6252482 | 9/1994 |
| WO | WO 92/15008 | 9/1992 |
| WO | WO 94/16622 | 8/1994 |
| WO | WO 96/07889 | 3/1996 |
| WO | WO 97/15229 | 5/1997 |
| WO | WO 98/44839 | 10/1998 |
| WO | WO 99/02939 | 1/1999 |

OTHER PUBLICATIONS

Goldstein, et al., The design and implementation of a high-fidelity Raman imaging microscope, Journal of Microscopy, vol. 184, Oct. 1996, pp. 35-45.

Kidder, et al., Mercury cadmium telluride focal-plane array detection for mid-infrared Fourier-transform spectroscopic imaging, Optics Letters, vol. 22, No. 10, May 15, 1997, pp. 742-744.

Kidder, et al., "Visualization of silicone gel in human breast tissue using new infrared imaging spectroscopy," Nature Medicine, vol. 3, No. 2, Feb. 1997, pp. 235-237.

Klonoff, "Noninvasive Blood Glucose Monitoring," Diabetes Care, vol. 20, No. 3, Mar. 1997, pp. 433-437.

Kohl, et al., "Influence of Glucose Concentration on Light Scattering in Tissue-Simulating Phantoms," Optics Letters, vol. 19, No. 24, Dec. 1994, pp. 2170-2172.

Lewis, et al., Fourier Transform Spectroscopic Imaging Using an Infrared Focal-Plane Array Detector, Analytical Chemistry, vol. 67, No. 19, Oct. 1, 1995, pp. 3377-3381.

Lewis, et al., High-Fidelity Fourier Transform Infrared Spectroscopic Imaging of Primate Brain Tissue, Applied Spectroscopy, vol. 50, No. 2, 1996, pp. 263-269.

Lewis, et al., Real-Time, Mid-Infrared Spectroscopic Imaging Microscopy Using Indium Antimonids Focal-Plane Array Detection, Applied Spectroscopy, vol. 49, No. 5, 1995, pp. 672-678.

Lewis, et al., Si: As Focal-Plane Array Detection for Fourier Transform Spectroscopic Imaging in the Infrared Fingerprint Region, Applied Spectroscopy. vol. 51. No. 4, 1997. pp. 563-567.

Mansfield. et al., "Fuzzy C-Means Clustering and Principal Component Analysis of Time Series from Near-Infrared Imaging of Forearm Ischemia," Computerized Medical Imaging and Graphics, vol. 21, No. 5, Sep.-Oct. 1997, pp. 299-308.

Mansfield, et al., "Analysis of Spectroscopic Imaging Data by Fuzzy C-Means Clustering," Analytical Chemistry, vol. 69, No. 16, Aug. 15, 1997, pp. 3370-3374.

McKenna, et al. "Integration of Visible/NIR Spectroscopy and Multispectral Imaging for Poultry Carcass Inspection", *Journal of Food Engineering* vol. 30, 1996, pp. 195-207.

Park, et al. "Integration of Visible/NIR Spectroscopy and Multispectral Imaging for Poultry Carcass Inspection," Journal of Food Engineering, vol. 30, 1996, pp. 195-207.

Qu, et al., "Monte Carlo Modeling Studies of the Effect of Physiological Factors and Other Analysis on the Determination of Glucose Concentration in Vivo by Near Infrared Optical Absorption and Scattering Measurements," Journal of Biomedical Optics, vol. 2, No. 3, Jul. 1997, pp. 319-325.

Schaeberle, et al., "Raman Chemical Imaging: Histopathology of Inclusions in Human Breast Tissue," Analytical Chemistry, vol. 68, No. Jun. 1, 1996, pp. 1829-1833.

Sowa, et al., "Noninvasive Assessment of Regional and Temporal Variations in Tissue Oxygenation by Near-Infrared Spectroscopy and Imaging," Applied Spectroscopy, vol. 51, No. 2 1997, pp. 143-152.

Strane, et al., "Assessment of Tissue Viability Using Near-Infrared Spectroscopy." British Journal of Plastic Surgery. 1998, pp. 210-217.

Waynant, et al., Overview of Non-Invasive Fluid Glucose Measurement Using Optical Techniques to Maintain GlucoseControl in Diabetes Mellitus, LEOS Newsletter, Apr. 1998, pp. 3-38.

Afromowitz et al., "Multispectral Imaging of Burn Wounds: A New Clinical Instrument for Evaluating Burn Depth." IEEE Trans Biomed Eng 1988; 35(10):842-50.

Hardin, R. Winn, "Hyperspectral Imaging: How Much is Hype?" Photonics Spectra, Jul. 1997, pp. 82-92.

Maier, et al., "Possible Correlation Between Blood Glucose concentration and the Reduced Scattering Coefficient of Tissues in the Near Infrared" Optics Letters, vol. 19, No. 24, Dec. 1994, pp. 2062-2064.

Williams, Roy E., et al., A Novel Method for Non-Invasive Multispectral Imaging of Tissue; IEEE; 291-294 (1992).

Bruulsema et al., "Correlation Between Blood Glucose Concentration in Diabetics and Noninvasively Measured Tissue Optical Scattering Coefficient," Optical Letters, vol. 22, No. 3, Feb. 1997, pp. 190-192.

Prahl et al., "Determination of optical properties of turbid media using pulsed photothermal radiometry," Phys. Med. Biol., 1992, vol. 37, No. 6, pp. 1203-1217.

\* cited by examiner

MULTISPECTRAL/HYPERSPECTRAL MEDICAL INSTRUMENT

CROSS-REFERENCES TO RELATED APPLICATIONS

The present application is a continuation of U.S. patent application Ser. No. 13/303,107, filed Nov. 22, 2011, which is a continuation of U.S. patent application Ser. No. 11/165,587, filed on Jun. 24, 2005, now issued as U.S. Pat. No. 8,175,688, which is a divisional of U.S. patent application Ser. No. 09/182,898, filed on Oct. 30, 1998, now issued as U.S. Pat. No. 6,937,885, which claims the benefit of U.S. Provisional Patent Application, Ser. No. 60/093,041, filed on Nov. 10, 1997, all which are hereby incorporated by reference in their entirety.

FIELD OF THE INVENTION

The invention relates to a surgical and diagnostic instrument for performing real-time general-purpose imaging during surgery, clinical procedures, or other medical evaluations.

BACKGROUND OF THE INVENTION

Spectroscopic imaging devices which employ Acousto-Optic Tunable Filters (AOTF), Liquid Crystal Tunable Filters (LCTF), or dispersive gratings are known. Such devices have been used for microscopy and remote sensing.

SUMMARY OF THE INVENTION

Generally, the invention features a medical instrument that includes an optic responsive to a surface of tissue of a patient, a spectral separator optically responsive to the optic, and an imaging sensor optically responsive to the spectral separator. The instrument also includes a diagnostic processor having an image acquisition interface responsive to the imaging sensor and a filter control interface to which the spectral separator is responsive.

The spectral separator can be a tunable filter, such as a liquid crystal tunable filter, and the imaging sensor can be a two-dimensional imaging array, such as a charge coupled device. The optic can include a macro lens, an adjustable lens, or a probe that includes an imaging fiber optic cable and a stand can be connected relative to the optic to position the optic relative to the patient. The control interface can be operable to adjust the filter at least twenty times to acquire hyperspectral data for redisplay in real time. The medical instrument can perform diagnostic processing for images acquired exclusively under visible light.

The diagnostic processor can also include a general-purpose processing module and diagnostic protocol modules, which can each include filter transfer functions and an image processing protocol. The general-purpose processing module can be operative to instruct the filter to successively apply the filter transfer functions to light collected from the patient, to acquire from the imaging sensor a number of images of the collected light each obtained after one of the filter transfer function is applied, and to process the acquired images according to the image processing protocol to obtain a processed display image. The general-purpose processor can be a real-time processor operative to generate a processed display image within a time period on the order of the persistence of human vision. It may also be operative to acquire some images more slowly depending on the number of wavelengths and complexity of diagnostic processing protocol. The sensor and filter can be operative in the visible, infra-red, and UV regions.

Instruments according to the invention are advantageous in that they can permit a surgeon or a physician to diagnose a medical condition or develop a surgical strategy based on real-time images obtained during surgery or in the course of performing clinical procedures or other medical evaluations. The physician may therefore be able to obtain significantly more information about a patient's condition than he might otherwise have been able to assemble by presenting an interactive interface. This additional information may permit a given surgical procedure to be carried out more precisely and may lead to more successful surgical results. It may also enhance the precision and results of other types of medical evaluations and procedures.

The general-purpose nature of the instrument can also help the surgeon develop significant amounts of medical information in time-critical surgical situations. For example, a patient may undergo relatively straight-forward surgery during which the surgeon may discover a tumor or another internal condition. With an instrument according to the invention, the physician can spend a small amount of additional time with the patient under anesthesia and determine the nature and extent of the tumor. This can be particularly beneficial during major surgery, where extending surgery duration poses a potential morbidity and mortality risk. Because the procedure is rapid and noninvasive, the patient is exposed to little additional risk. The benefit of immediate diagnosis and evaluation is significant.

An instrument according to the invention may also be able to provide a wide variety of diagnostic capabilities, allowing a physician to enhance the capabilities of his or her practice substantially in a variety of different realms, without investing in a number of instruments. The physician can then enhance or update the instrument by the adding software modules that are specifically targeted towards certain conditions of particular tissues, subsystems, or disease states. This can allow a single base instrument to be configured for a variety of different types of practices, and priced according to the type of practice to be served by the instrument. For example, a general-purpose instrument to be used by a general surgeon could include a package of diagnostic protocols that would permit the diagnosis of a variety of conditions that a general surgeon might encounter, while a neurosurgeon's module might be added to allow a specialist to detect particular conditions within the brain. Electronic and optical upgrades may also be provided to update, specialize, or improve the performance of the instrument. Such upgrades can include processing modules, memory boards, lenses, and the like.

DETAILED DESCRIPTION OF AN ILLUSTRATIVE EMBODIMENT

Figure 1:
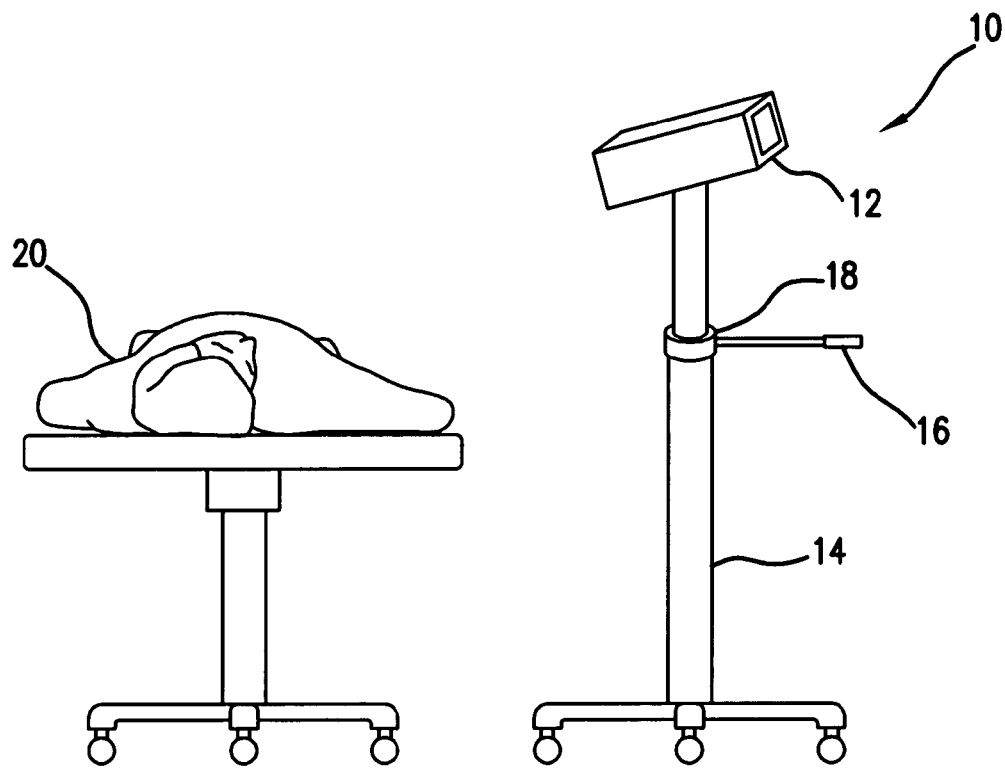
FIG. 1 is a perspective diagram of a macroscopic instrument according to the invention.

Referring to FIG. 1, an instrument according to the invention 10 includes an imaging module 12 mounted on a surgical stand 14. In this embodiment, the surgeon can direct the imaging portion 12 towards a patient 20 by manipulating a control 16 that adjusts the attitude of the imaging portion through a positioning mechanism 18.

Figure 2:
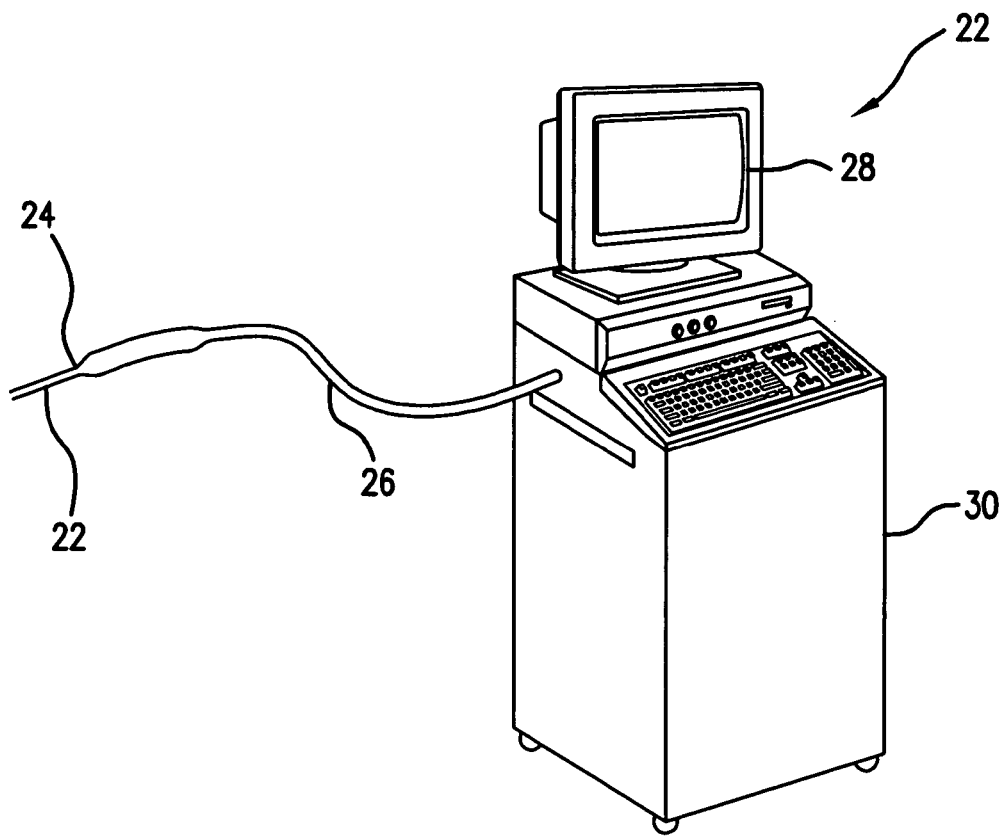
FIG. 2 is a perspective diagram of a rigid or flexible probe-based instrument according to the invention.

Referring to FIG. 2, an alternative embodiment of the invention 22 may include a probe such as a rigid or flexible endoscopic, thoracoscopic, laproscopic, or angioscopic probe 24 connected to an imaging station 30 via a fiber optic cable 26. The surgeon can manipulate the probe within the patient in a minimally-invasive surgical procedure and derive images from a portion of the patient and display these images on a display 28. A medical implement 32, such as a laser, can also be provided through the probe. For example, after diagnosing a particular condition, a physician can begin laser ablation therapy to remedy it.

Figure 3:
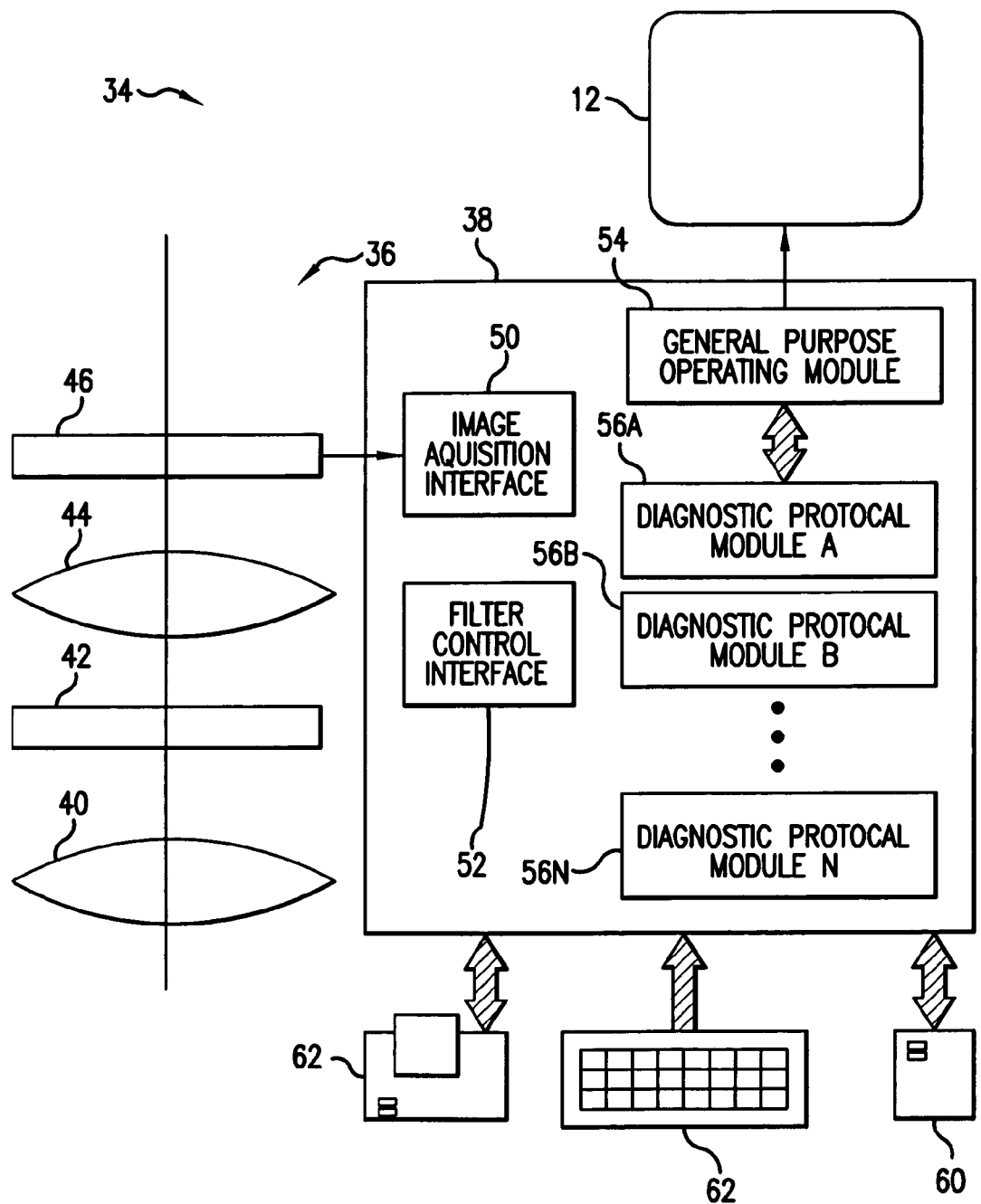
FIG. 3 is a block diagram of the instrument of FIG. 1.

Referring to FIG. 3, a medical instrument according to the invention 34 may include an optical acquisition system 36 and a diagnostic processor 38. The acquisition system 36 includes a first-stage imaging optic 40, a Liquid-Crystal Tunable Filter (LCTF) 42, a second-stage optic 44, and an imaging element 46. The first-stage optic receives light collected from the patient and focuses it onto the surface of the LCTF. The first-stage optic can be a simple or compound macro lens in the case of a macroscopic instrument (FIG. 1). In a probe-based instrument (FIG. 2), the first stage optic can include imaging optics within a probe such as a endoscopic, laproscopic, thoracoscopic, or angioscopic probe. The first stage lens can also be adjustable, allowing a physician to scan larger areas of tissue and then zoom into particular regions.

The LCTF 42 is a programmable filter that filters out all but a wavelength region of interest from the light collected from the patient. The second-stage optic 44 receives the remaining light from the LCTF and focuses it onto the image sensor 46. The image sensor is preferably, although not necessarily, a two-dimensional array sensor, such as a charge-coupled device array (CCD), which delivers an image signal to the diagnostic processor 38.

The diagnostic processor 38 includes an image acquisition interface 50, that has an input responsive to an output of the image sensor 46 and an output provided to a general-purpose operating module 54. The general-purpose operating module includes routines that perform image processing, and that operate and control the various parts of the system. It has a control output provided to a filter control interface 52, which in turn has an output provided to the LCTF 42. The general-purpose operating module also interacts with a number of diagnostic protocol modules 56A, 56B, . . . , 54N, and has an output provided to the video display 12. The diagnostic processor can include special purpose hardware, general-purpose hardware with special-purpose software, or a combination of the two. The diagnostic processor also includes an input device 58, which is operatively connected to the general-purpose operating module. A storage device 60, and a printer are also operatively connected to the general-purpose operating module.

Figure 4:
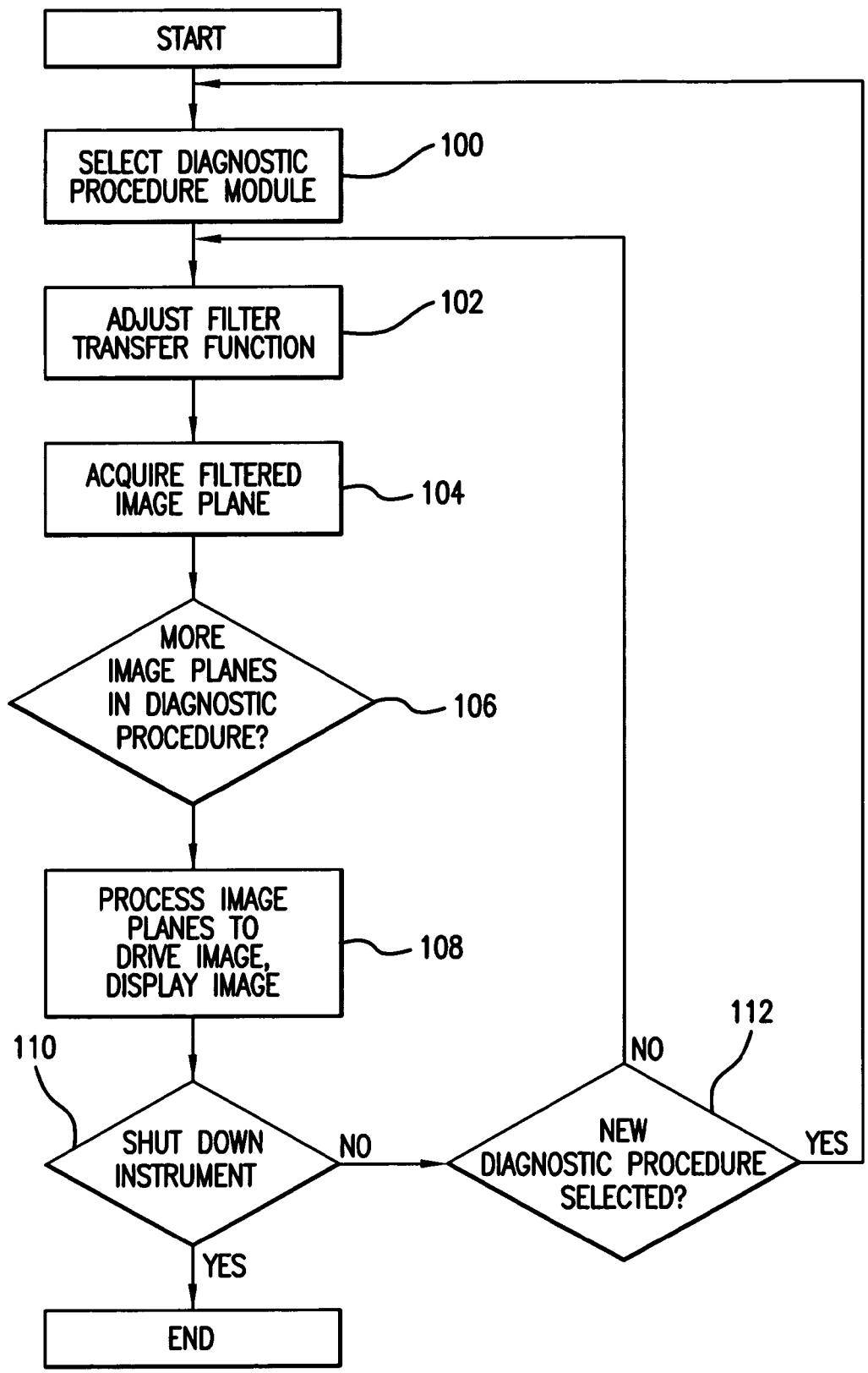
FIG. 4 is a flowchart illustrating the operation of the system of FIG. 1.

In operation, referring to FIGS. 3 and 4, a surgeon employing the instrument begins by selecting a diagnostic protocol module using the instrument's input device (step 100). Each diagnostic protocol module is adapted to detect particular characteristics of the surface of one or more types of tissue. For example, the surgeon might select a module which enhances the visibility of cancerous tissue. The surgeon would then direct the camera at the area of interest and begin inspecting it either under ambient light or with the aid of a supplemental light source, which can be filtered to emphasize particular special characteristics of the light it emits.

The diagnostic processor 38 responds to the surgeon's input by obtaining a series of filter transfer functions and an image processing protocol from the selected diagnostic protocol module 56. The diagnostic processor provides the filtering transfer functions to the LCTF 42 via its filter control interface 52 (step 102) and then instructs the image acquisition interface 50 to acquire and store the resulting filtered image from the image sensor 46 (step 104). The general-purpose operating module 54 repeats these filtering and acquiring steps one or more times, depending on the number of filter transfer functions stored in the selected diagnostic protocol module (see step 106). The filtering transfer functions can represent bandpass, multiple bandpass, or other filter characteristics.

Once the image acquisition interface 50 has stored images for all of the image planes specified by the diagnostic protocol chosen by the surgeon, it begins processing these image planes based on the image processing protocol from the selected diagnostic protocol module 56N (step 108). Processing operations can include general image processing of combined images, such as comparing the relative amplitude of the collected light at different wavelengths, adding amplitudes of the collected light at different wavelengths, or computing other combinations of signals corresponding to the acquired planes. The processing operations can also include more complex multivariate statistical techniques to compute the image (e.g., chemometrics). The computed image is displayed on the display 12. It can also be stored in the storage device 60 or printed out on the printer 62.

The processing operations can also be based on a diagnostic knowledge base. This database can include data resulting from the comparison between optical and actual diagnoses. Each instrument can also continuously update its database as it is used to perform diagnoses, thereby steadily expanding its diagnostic capabilities.

In order to provide a real-time or near-real-time image to the surgeon, the instrument repeatedly acquires planes and processes them to develop an image to be displayed to the surgeon. This allows the surgeon to move the instrument, or to view moving organs, such as a beating heart. This constant acquisition and processing continues until the surgeon either turns the instrument off (step 110) or selects a different imaging mode (step 112). The diagnostic processor 38 preferably has sufficient processing power to update the screen in this way at video rates (i.e., about 30 frames per second), although rates as low as a few frames per second may work quite well, and rates as low as one frame per minute may be adequate for many purposes. On slower instruments, general lock-in schemes or other tracking modalities, such as cardiac gating, can be used to remove motion artifacts due to breathing or heart beat. Frame rate may also be variable, depending on the number of wavelengths and the complexity of the diagnostic procedure.

Preferably, the instrument can operate in multispectral, and hyperspectral, or even ultraspectral imaging modes. Multispectral modes involve image processing derived from a relatively small number of spectral image planes (two wavelengths to about twenty wavelengths). Hyperspectral and ultra spectral imaging modes involve at least twenty image planes and can produce significantly more accurate and informative results. Ultraspectral modes involve hundreds of wavelengths, and may be able to produce even further information about the patient. Hyperspectral and ultraspectral imaging may include selecting specific wavelength bands for discrimination of a particular diseased states, or it may also allow the instrument to scan for multiple conditions at the same time.

It is also contemplated that both types of instrument can operate in connection with an excitation source, such as an ultraviolet lamp and IR source, or other means of spectral illumination or a laser to enhance the received images. Although such excitation may not be necessary, it may allow for the examination of different optical phenomenon and provide additional diagnostic information. And both emission and reflectance modes can be combined in a diagnostic procedure either simultaneously or sequentially. Relative utilization of different emission or reflection measurements involved in the same diagnostic procedure can be obtained by modulating the different sources. The instrument can also develop light from bioluminescent sources introduced into the patient.

Instruments according to the invention can also operate to process images from image planes acquired at wavelengths outside of the visible region. In one particular embodiment, the instrument is sensitive to the visible and near infra-red regions. It is also contemplated that far infra-red be included to allow the instrument to sense molecular-specific rotational modes.

An example of operation would include the use of a diagnostic protocol module that examined a first wavelength of about 550 and a second wavelength of about 575 associated with oxy- and deoxy-hemoglobin to determine blood oxygenation. The relationship between these wavelengths is described in "Hemoglobin: Molecular Genetics and Clinical Aspects," by H. Franklin Bunn and Bernard Forget, W. B. Sanders, 1986. Another example would include the use of a diagnostic protocol module for examining the Fourier transform infra-red spectra of the colon and rectum as described in "Human Colorectal Cancers Display Abnormal Fourier Transform Spectra," by Basil Rigas et al., Proceedings of the National Academy of Science, pp. 8140-8144, 1987.

Surgical and medical applications of instruments according to the invention can include, but are not limited to, determining tissue viability (i.e. whether tissue is dead or living tissue and whether it is predicted to remain living), detecting tissue ischemia (e.g., in heart, or in leg after a gunshot wound, differentiating between normal and malignant cells and tissues (e.g., delineating tumors, dysplasias and precancerous tissue, detecting metastasis), differentiating between of infected and normal (but inflamed) tissue (e.g., extent of aortic root infection), quantification and identification of pathogens, (e.g., bacterial count of burn wounds and differentiating and delineating other pathologic states. Application can also include tissue, blood chemistry, and blood flow (including oxy- and deoxyhemoglobin, myoglobin deoxymyoglobin, cytochrome, pH, glucose, calcium and other elements or biological compounds alone or in combination). The instrument can also be applied by veterinarians to animals and by dentists to dental applications, such as peridental disease.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

The invention claimed is:

1. A multispectral or hyperspectral medical instrument comprising:
   (A) an optical acquisition system (36) comprising an image sensor (46) that is configured to acquire multispectral, hyperspectral, or ultraspectral images; and
   (B) a diagnostic processor (38) comprising:
      (i) a general-purpose operating module (54) having output to a display,
      (ii) an image acquisition interface (50) having an input responsive to the output of the image sensor (46) and further having an image acquisition interface output that is provided to the general-purpose processing module, and
      (iii) instructions for applying any one of a plurality of diagnostic protocol modules (56) to the image acquisition interface output provided from the image acquisition interface (50), wherein each respective diagnostic protocol module in the plurality of diagnostic protocol modules includes instructions to acquire a plurality of image planes using optical acquisition system (36) and an image processing protocol with instructions to process the plurality of image planes to enhance visualization of a particular characteristic of the surface of one or more types of tissue, through the application of filtering and acquiring instructions associated with the respective diagnostic protocol.

2. The multispectral or hyperspectral medical instrument of claim 1, wherein the optical acquisition system (36) comprises a first-stage imaging optic (40) in optical communication with the image sensor (46), the first-stage imaging optic including an adjustable lens.

3. The multispectral or hyperspectral medical instrument of claim 1, wherein the image sensor (46) is a two dimensional imaging array.

4. The multispectral or hyperspectral medical instrument of claim 1, wherein the image sensor (46) comprises a charge coupled device (CCD).

5. The multispectral or hyperspectral medical instrument of claim 1, wherein the image sensor (46) is sensitive to the visible region of the electromagnetic spectrum.

6. The multispectral or hyperspectral medical instrument of claim 1, wherein the image sensor (46) is sensitive to the near infra-red region of the electromagnetic spectrum.

7. The multispectral or hyperspectral medical instrument of claim 1, wherein the image sensor (46) is sensitive to the visible and near infra-red regions of the electromagnetic spectrum.

8. The multispectral or hyperspectral medical instrument of claim 1, wherein the image sensor (46) is sensitive to the far infra-red region of the electromagnetic spectrum.

9. The multispectral or hyperspectral medical instrument of claim 1, wherein the general-purpose operating module (54) is operative to generate a processed display image between one time a second and thirty times a second.

10. The multispectral or hyperspectral medical instrument of claim 1, wherein the diagnostic processor (38) is modular and upgradeable by adding additional diagnostic protocol modules (56), thereby expanding diagnostic capabilities.

11. The multispectral or hyperspectral medical instrument of claim 1, wherein the diagnostic processor (38) further comprises a diagnostic database including data resulting from comparison of collected multispectral or hyperspectral images and actual diagnoses.

12. The multispectral or hyperspectral medical instrument of claim 11, wherein the diagnostic database is updatable upon use by a clinician, thereby expanding a diagnostic capability of the diagnostic processor (38).

13. The multispectral or hyperspectral medical instrument of claim 1, wherein each respective diagnostic protocol module in the plurality of diagnostic protocol modules (56) further includes instructions to process a plurality of images acquired by the image sensor (46) to obtain a multispectral or hyperspectral image.

14. The multispectral or hyperspectral medical instrument of claim 13, wherein the processing of the plurality of images acquired by the image sensor (46) includes the use of multivariate statistical techniques.

15. The multispectral or hyperspectral medical instrument of claim 1, wherein the particular characteristic of the surface of one or more types of tissue is the viability of a tissue.

16. The multispectral or hyperspectral medical instrument of claim 1, wherein the particular characteristic of the surface of one or more types of tissue is tissue ischemia.

17. The multispectral or hyperspectral medical instrument of claim 1, wherein the particular characteristic of the surface of one or more types of tissue is a malignant cell or tissue.

18. The multispectral or hyperspectral medical instrument of claim 1, wherein the particular characteristic of the surface of one or more types of tissue is oxyhemoglobin and deoxyhemoglobin.

19. The multispectral or hyperspectral medical instrument of claim 1, further comprising a probe (24) connected to the optical acquisition system (36) via a fiber-optic cable (26).

20. The multispectral or hyperspectral medical instrument of claim 19, wherein the probe (24) is a rigid endoscopic probe, a flexible endoscopic probe, a thoracoscopic probe, a laproscopic probe, or an angioscopic probe.

\* \* \* \* \*